United States Patent [19]

Taboada et al.

[11] Patent Number: 4,896,015
[45] Date of Patent: Jan. 23, 1990

[54] LASER DELIVERY SYSTEM

[75] Inventors: John Taboada; Robert H. Poirier, both of San Antonio, Tex.

[73] Assignee: Refractive Laser Research & Development Program, Ltd., San Antonio, Tex.

[21] Appl. No.: 226,287

[22] Filed: Jul. 29, 1988

[51] Int. Cl.[4] .............................................. B23K 26/00
[52] U.S. Cl. .......................... 219/121.78; 219/121.79; 219/121.84
[58] Field of Search ........... 219/121.6, 121.85, 121.78, 219/121.74, 121.84, 121.8, 121.63, 121.64, 121.67, 121.72, 29; 384/12, 13

[56] References Cited

U.S. PATENT DOCUMENTS

| 3,166,361 | 1/1965 | Panzer et al. | 384/29 |
| 3,913,582 | 10/1975 | Sharon | 128/303.1 |
| 3,528,424 | 9/1970 | Ayres | 128/303.1 |
| 3,658,406 | 4/1972 | Karube et al. | 350/52 |
| 3,663,071 | 5/1972 | Kates | 384/12 |
| 4,473,074 | 9/1984 | Vassiliadis | 219/121.74 X |
| 4,623,229 | 11/1986 | Galan | 219/121.63 X |

Primary Examiner—C. L. Albritton
Attorney, Agent, or Firm—Mason, Fenwick & Lawrence

[57] ABSTRACT

A laser delivery system comprises a light weight hollow boom having a bearing intermediate its ends which permits the distal end of the boom to move longitudinally and rotationally relative to the proximal end of the boom. The bearing supports the distal end without supporting physical contact, e.g. by a layer of fluid. The proximal end of the boom is carried by a boom support for movement about two axes, and includes a fork journalled in a base. In one embodiment, the shaft has a portion offset from the axis thereof, and a beam direction changer, such as a prism, is located along the shaft axis between spaced bearings journalling the shaft and carried by the base. In a second embodiment, a light conducting passage extends completely through the shaft. A handpiece is connected to the distal end of the boom for rotation about the boom axis. The boom is counterbalanced by a first counterweight in offset relation to the boom axis relative to the shaft axis, and on the opposite side from the boom of the pivotal axis transverse to the boom. A second smaller counterweight is between the boom support and the boom bearing, with its center of gravity on the boom axis, and a third counterweight smaller than the second is between the boom bearing and the handpiece, on the opposite side of the boom axis from the handpiece.

43 Claims, 4 Drawing Sheets

LASER DELIVERY SYSTEM

TECHNICAL FIELD

The present invention relates to a laser delivery system, including a tubular boom, a handpiece, and a support for the boom.

BACKGROUND ART

Lasers have become widely used for industrial and medical applications. In many instances, the laser beam emitted by the laser apparatus is passed through a handpiece or other final delivery implement which is required to be manipulated so as to direct the laser beam in a precise manner. Various delivery system have heretofore been proposed, including both articulated booms and linear booms which are nonarticulated, the laser beam entering the proximal end of the boom, passing through the boom and into the proximal end of the handpiece.

Ayres U.S. Pat. No. 3,528,424 discloses a laser apparatus for use in surgery, there being provided a first right-angle conduit having a reflector at the angle and located about the arm connected to the laser housing, a second right-angle conduit rotatably connected to the second leg of the first right-angle conduit, and a linear boom connected at its proximal end to the second leg of the second right-angle conduit. The boom comprises first and second telescopic parts, the latter supported for rotational and longitudinal movement by a boom bearing comprising a pair of axially spaced ball bearings. At the distal end of the boom, a second joint made up of two right-angle conduits is provided, there being connected to the second leg of the second right-angle conduit a connection for a handpiece permitting rotation of the handpiece about an axis transverse to the second leg of the second right-angle conduit. A spring is connected to the outer part of the boom, for counterbalancing. This structure does not disclose a strong pivotal support for the proximal end of the boom, and provides a boom bearing which is somewhat resistant to movement, and therefore causes movement of the handpiece to be accomplished with more resistance to movement than is desirable, and there is provided a less than satisfactory counterbalancing system.

Vassiliadis U.S. Pat. No. 4,473,074 provides a surgical laser apparatus having a laser head supported by an articulated support arm system extending from a post. From the laser head, there extends a multi-section boom with a base section having a boom bearing formed by outer and inner tubes, the inner tube being supported for longitudinal and rotational movement by spaced apart groups of balls carried by a sleeve intermediate the two tubes. An intermediate boom section is connected to the base boom section by a joint permitting movement on an axis perpendicular to the boom base section axis, and a handpiece is connected to the intermediate boom section by a similar joint. The mounting of the boom to the laser head is fixed, no counterbalancing is shown, and the bearing, utilizing balls, offers more resistance than is desirable.

Sharon U.S. Pat. No. 3,913,582 provides a laser device which includes an optical bench having a laser within it, the bench being supported near one end on a post extending from a base cabinet. An upstanding shaft extends from the distal end of the optical bench, having a horizontally extending sleeve bearing on which is mounted a housing with a reflector in it, a longitudinally extending boom section being connected to the housing, and having at its distal end two right-angle conduits, with mirrors in them, the second conduit being connected to a second boom section which, at its distal end, has a triple right-angle conduit connection to a handpiece. A single counterbalance weight is provided on an arm which is supported on a horizontal pivot at the end of the shaft, one arm of the counterbalance engaging the first boom section, and the other arm supporting a counterweight. This apparatus does not have an axially extendable boom section, has no disclosure of the support structure for the proximal end of the boom, and has only a single counterweight to counterbalance all of the portions of the support arm system.

Karube et al U.S. Pat. No. 3,658,406 provides a laser beam guide apparatus in which a laser emitting device has a stationary boom connected to it, the boom having at its distal end a gear box to which a moving boom or handpiece is rotatably connected, there being a gear driven mirror within the gear box. The stationary boom contains a roller bearing permitting relative axial and rotational movement between two telescopic parts thereof. There is no disclosure of the mounting for the first boom section, which is rigidly fixed to the emitting device, the boom bearing has more friction than is desirable, and no counterbalancing is provided.

Galan U.S. Pat. No. 4,623,229 provides an articulated laser arm apparatus for use with a robot, for industrial purposes. A four-section boom is connected to a laser; the first and second sections are fixed. The second section is rotatably connected by a right-angle joint to the third section, and the third section is rotatably connected by a pair of right-angle joints to the fourth section, with a pair of mirrors therein. The distal end of the fourth section is connected to a pair of right-angle joints, utilizing three reflectors, to the last of which is connected a laser delivery instrument guided by a robot. A counterbalance mechanism is provided comprising a pair of spaced apart bunges (counterbalance springs) which are connected at their lower ends to the fourth section of the boom, and at their upper ends to a fixed support. This construction requires multiple articulated boom sections, there is no extendable boom section, and the counterbalancing is effective only with regard to the entire mass of the boom, starting with the third section and to the utilization implement, so that counterbalancing is less exact than is desirable for a hand held utilization implement or handpiece.

SUMMARY OF THE INVENTION

The present invention laser delivery system includes a base adapted to be mounted on a support, such as cart, a linearly extending boom carried by the base and a handpiece carried by the boom. The proximal end of the boom is supported on the base for movement about a first axis by a shaft journalled in the base by a pair of spaced bearings, the shaft carrying at one end a fork to which is journalled a boom support for pivotal movement about a second axis transverse to the first axis. The boom is attached to the boom support, the boom axis being transverse to the axis through bearings journalling the boom support on the fork; the axis of the bearings in the base is transverse to the axis through the boom support bearings, but offset from the boom axis. In one embodiment, the shaft is cranked, having an offset portion, and a beam direction changer, such as prism, is positioned between two aligned portions of the shaft which extend through the bearings; this prism changes the direction of the beam which has entered the base transverse to the bearing axis, so that the boom passes through a portion of the shaft journalled in one of the bearings in the base. The beam is directed into the boom by a pair of direction changers after passing through the shaft. In a second embodiment, the shaft has an opening from end to end, through which the beam passes to a pair of direction changers.

The boom is light weight and comprises a pair of tubular members, the member forming the distal part of the boom being smaller in diameter and being supported in the proximal larger diameter tubular member by a bearing permitting linear and rotational movement of the distal tubular member relative to the proximal tubular member: a cushion or layer of fluid, such as gas, is supplied to the space between the proximal and distal boom members, and provides the support for the distal boom member. The handpiece is connected to the boom by a connection permitting rotational movement of the handpiece about an axis transverse to the boom axis, and the lower portion of the handpiece may be rotated on the axis of the handpiece.

A counterbalancing system for the boom is provided including a first relatively large counterweight mass supported on the opposite side from the boom of the axis which passes through the bearings in the boom support, and also is displaced oppositely to the boom relative to the axis which passes through the bearings in the base. A second counterweight mass smaller than the first is provided on the proximal tubular member, preferably encircling the proximal tubular member so that the center of gravity of the second mass is substantially at the boom axis. A third counterweight mass, smaller than the second counterweight mass, is provided on the distal end of the boom, offset from the boom axis oppositely to the offset of the handpiece from the boom axis.

Among the objects of the present invention are the provision of a laser delivery system including a handpiece through which a laser beam is passed, which handpiece may be moved to any required position and direction with minimal effort.

Yet another object of the present invention is to provide a laser delivery system in which a lightweight tubular boom is mounted for movement about two axes, while supported by a rigid two-axis pivotal construction.

Yet another object of the present invention is the provision of a laser delivery system in which telescopic movement of a boom may be made with negligible frictional resistance.

Still another object of the present invention is the provision of a laser delivery system which includes a boom and handpiece which are substantially counterbalanced by multiple component counterbalancing system.

Others objects and many of the attendant advantages of the present invention will be readily apparent from the following specification, drawings and claims.

DESCRIPTION OF THE PREFERRED EMBODIMENTS

Figure 1:
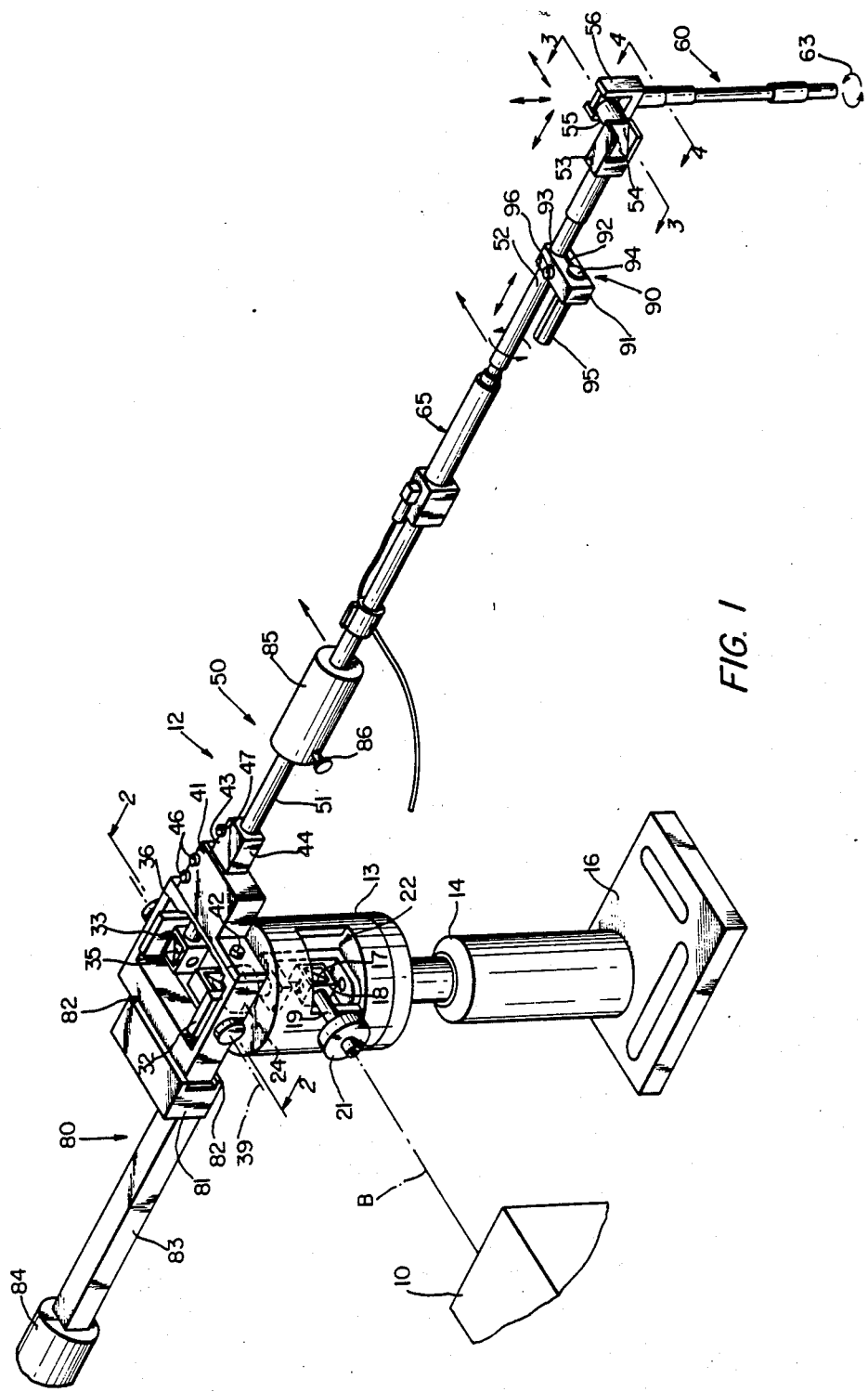
FIG. 1 is a perspective view of a first embodiment of a laser delivery system in accordance with the present invention.

Referring now to the drawings, wherein like or corresponding reference numerals are used for like or corresponding parts throughout the several views, there is shown in FIG. 1 a laser apparatus 10 which emits a laser beam B. A laser delivery system 12 is provided for receiving the laser beam B, and for delivering it to a point of use, the laser delivery system 12 including a hollow cylindrical base 13 carried by a post 14 that is secured by an adjustable bracket 16 to a suitable support, such as a table or movable cart: as will be understood, the laser apparatus 10 will also be carried by the same table or cart.

A prism 17 is supported in a fixture 18 carried on a tubular shaft 19 which extends through an opening in the wall of the base 13. The shaft 19 may be moved along its axis, and rotated on its axis, and then held by clamp 21 in the desired position to receive and reflect the beam B at an angle of 90°.

Figure 2:
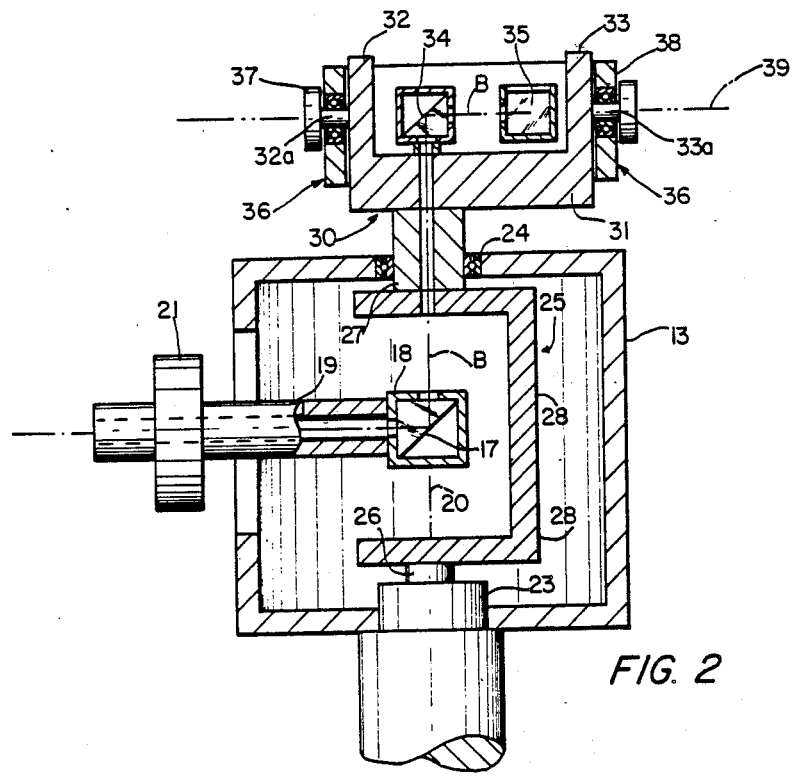
FIG. 2 is a cross-sectional view, taken on the line 2—2 of FIG. 1.

As shown in FIG. 2, there is provided in the hollow base 13 a lower bearing 23 and an upper bearing 24 which support a cranked shaft 25. The cranked shaft 25 has a first portion 26 supported by the lower bearing 23 and a second portion 27 aligned with the portion 26, supported in the upper bearing 24. An offset or cranked portion 28 connects the shaft portions 26 and 27. As is apparent from FIG. 2, prism 17 lies along the axis 20 of shaft portions 26 and 27, its positioning being permitted by the cranked nature of the shaft 25, and the shaft 25 may rotate through a substantial arc without engagement of the cranked or offset portion 28 with the shaft 19.

The portion 27 of cranked shaft 25 supports a fork 30 having a first portion 31 transverse to the shaft portion 27, and a pair of spaced tines 32 and 33 which carry between them a pair of spaced prisms 34 and 35. Prism 34 is in alignment with prism 17 and prism 35, and a prism 35 is in alignment with boom 50 (see FIG. 1).

As shown in FIG. 1, a boom support 36 is of generally hollow rectangular configuration, supported by bearings 37 and 38 therein which receive pins 32a and 33a extending from the tines 32 and 33 respectively, so that the boom support 36 may rotate about an axis 39 through the bearings 37 and 38.

An right-angle connector piece 41 is secured to the boom support 36 for adjustment parallel to the axis 39, being secured in place by a screw 42 or other similar locking element. The connector piece 41 has a recess 43 to receive a block 44 to which the proximal end of the boom 50 is connected. Clamping screws 46 secure the block 44 in the connector piece 41, and a set screw 47 secures the boom 50 in the block 44.

Figure 3:
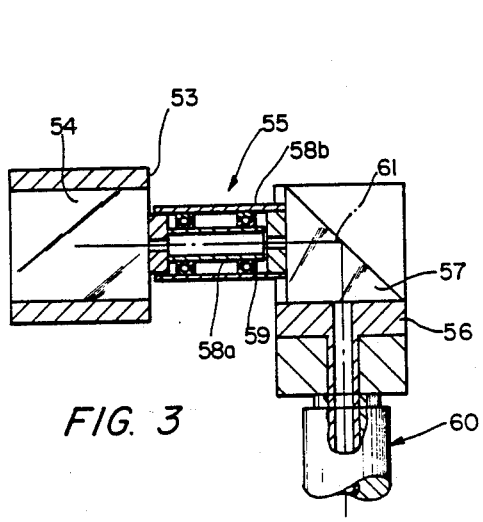
FIG. 3 is a cross-sectional view, taken on the line 3—3 of FIG. 1.

Boom 50 comprises a tubular outer boom member 51 and a tubular inner boom member 52. As will be apparent, the proximal end of boom 50 is secured to the boom support 36, and the boom 50 at its distal end has connected to it a handpiece 60. Intermediate its ends, the boom 50 is provided with a boom bearing 65. At its distal end, the boom 50 is provided with a fork 53 having therein a prism 54. As shown in FIG. 3, a joint assembly 55 provides a rotary connection between the fork 53 and a second fork 56, the latter supporting a prism 57. The joint assembly includes inner and outer tubes 58a and 58b attached to the forks 53 and 56, journalled by bearings 59. Joint 55 provides a connection by which the handpiece 60 is connected to the boom 50, so that it may rotate about an axis 61 which is transverse to the axis of the boom 50.

Figure 4:
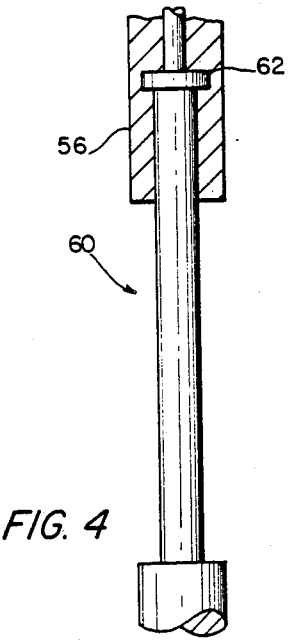
FIG. 4 is a cross-sectional view, taken on the line 4—4 of FIG. 1.

As shown in FIG. 4, the handpiece 60 extends into the hollow stem of the fork 56, where a bearing 62 permits rotation of handpiece 60 on the longitudinal axis thereof: see the arrow 63 in FIG. 1.

Figure 5:
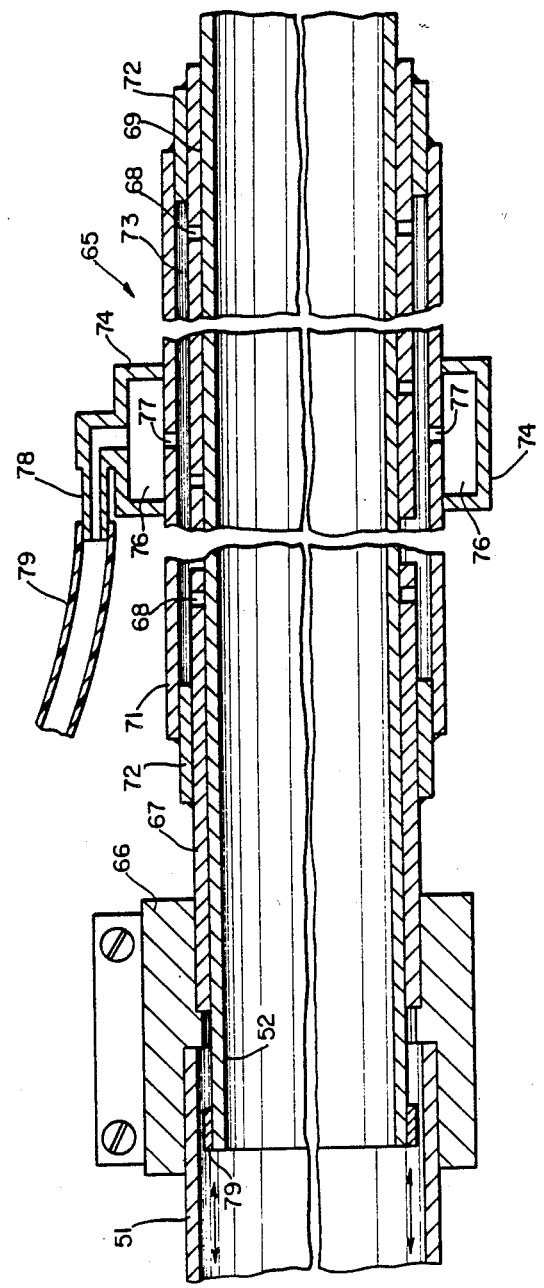
FIG. 5 is a cross-sectional view, taken on the line 5—5 of FIG. 1.

The boom bearing 65 and related parts are shown in FIG. 5, where there may be seen the tubular outer boom member 51 and the tubular inner boom member 52 telescopically therewithin. More particularly, a collar 66 connects the tubular outer boom member 51 with the outer boom member extension 67 which is provided with a series of small apertures 68 which are distributed radially and longitudinally thereover. The inner diameter of the outer boom member extension 67 is slightly larger than the outer diameter of the tubular inner boom member 52, so that there is a space or clearance between them. An outer jacket 71 is attached, as by welding, to a pair of spaced sleeves 72, which are in turn secured, as by welding, to the outer boom member extension 67. Between the jacket 71 and the outer boom member extension 67 is a plenum chamber. An annular supply jacket 74 of limited axial extent is positioned circumferentially about and attached to the jacket 71, and provides a supply chamber 76, connected to the plenum chamber 73 by apertures 77. The supply chamber has attached to it a nipple 78 to which is connected a flexible tube 79, which supplies fluid, specifically air or some other gaseous material such as an inert gas, from a source connected to the opposite end of the tube 79. The proximal end of the tubular inner boom member 52 is provided with a retaining ring 79 of larger diameter than the inner diameter of the outer boom member extension 67.

In practice, the apertures 68 and the apertures 77 may be 0.5 mm in diameter, and there may be twenty-four apertures 68. The gas or air pressure may be 20 psi, and when supplied to the boom bearing 65, the tubular inner boom member 52 is supported by a cushion or layer of fluid between it and the outer boom member extension 67, permitting it to be moved both rotationally and longitudinally without significant friction. Consequently, there being no supporting physical engagement of inner boom member 52, manipulation of the handpiece 60 to cause movement of the tubular inner boom member 52 relative to the tubular outer boom member 51 is without perceptible resistance. The fluid is discharged through annular openings at the ends of the outer boom member extension 67.

To provide for precise counterbalancing of the boom 50, including the handpiece 60, there are provided, as shown in FIG. 1, a counterweight 80, including a support block 81 having a pair of rails 82 which receive a portion of the boom support 36 for adjusting movement parallel to the axis 39. Suitable means (not shown) are provided for securing the support block 81 in the desired position. Extending from the support block 81 is an arm 83 having adjustably longitudinally positioned thereon a counterweight mass 84. The arm 83 will be seen to extend oppositely, relative to the axis 39, to the boom 50, and will also be seen to extend oppositely relative to the axis 20 through the bearings 23 and 24 from the boom 50: that is, boom 50 and arm 83 are oppositely offset relative to the axis 20 of the bearings 23 and 24.

A second counterweight 85 is provided upon the tubular outer boom member 51, being a mass in the shape of a hollow cylinder having the inner diameter slightly larger than the outer diameter of the tubular outer boom member 51. Thus, the center of gravity of the counterweight mass 85 is substantially at the axis of the boom 50; counterweight mass 85 may be moved longitudinally of boom 50, and secured in position by a set screw 86.

A third counterweight 90 is secured to the tubular inner boom member 52 which forms the distal end of the boom 50; it comprises a clamp block 91 having a split 92 and a passage 93 for receiving the tubular inner boom member 52 and an opening 94 for receiving a counterweight mass 95. A set screw 96 is provided to secure the counterweight 90 in the desired position on tubular inner boom member 52, both longitudinally and circumferentially. The counterweight 90 will be understood to have the center of gravity thereof spaced from the axis of boom 50 oppositely to the center of gravity of the handpiece 60 and the connector member 55, to thereby provide a counterbalance specifically for the means of these elements.

In use, a beam B from the laser 10 will be directed into the base 13 through an opening therein passing through the shaft 19, and being reflected by prism 17 so that it passes along the axis 20 of the shaft 25 to the prism 34. It is there reflected to the prism 35, and thence into the boom 50, passing along the axis thereof to the prism 54, where it is reflected through the connector 55 to the prism 57, which directs the beam B axially into the handpiece 60. The handpiece 60 may be manipulated, so as to rotate the boom 50 about the axis of the shaft 25, and also rotate it about the axis 39. In addition, handpiece 60 may be rotated about the axis of boom 50, and moved towards and away from the base 13, without significant frictional resistance, due to the boom bearing 65 which utilizes a cushion of air or other gas. The handpiece 60 may also be rotated about the axis 61, extending through the connector 55, and the distal end of the handpiece 60 may be rotated about its axis as indicated by the arrows 63. Due to the precision counterbalancing provided by counterweights 80, 85 and 90, all of such movements are easily precision made, without significant effort or force. Thus, the handpiece 60 is substantially as manipulable as an independently held scalpel or other independent instrument. In addition, due to the noted construction utilizing a single linear boom, the boom 50 is of low weight, adding to its ability to be manipulated, along with the handpiece 60. Further, because of the very small connection of handpiece 60 to the boom 50, there is little or no obstruction to the viewing of the operational site by the surgeon.

Figure 6:
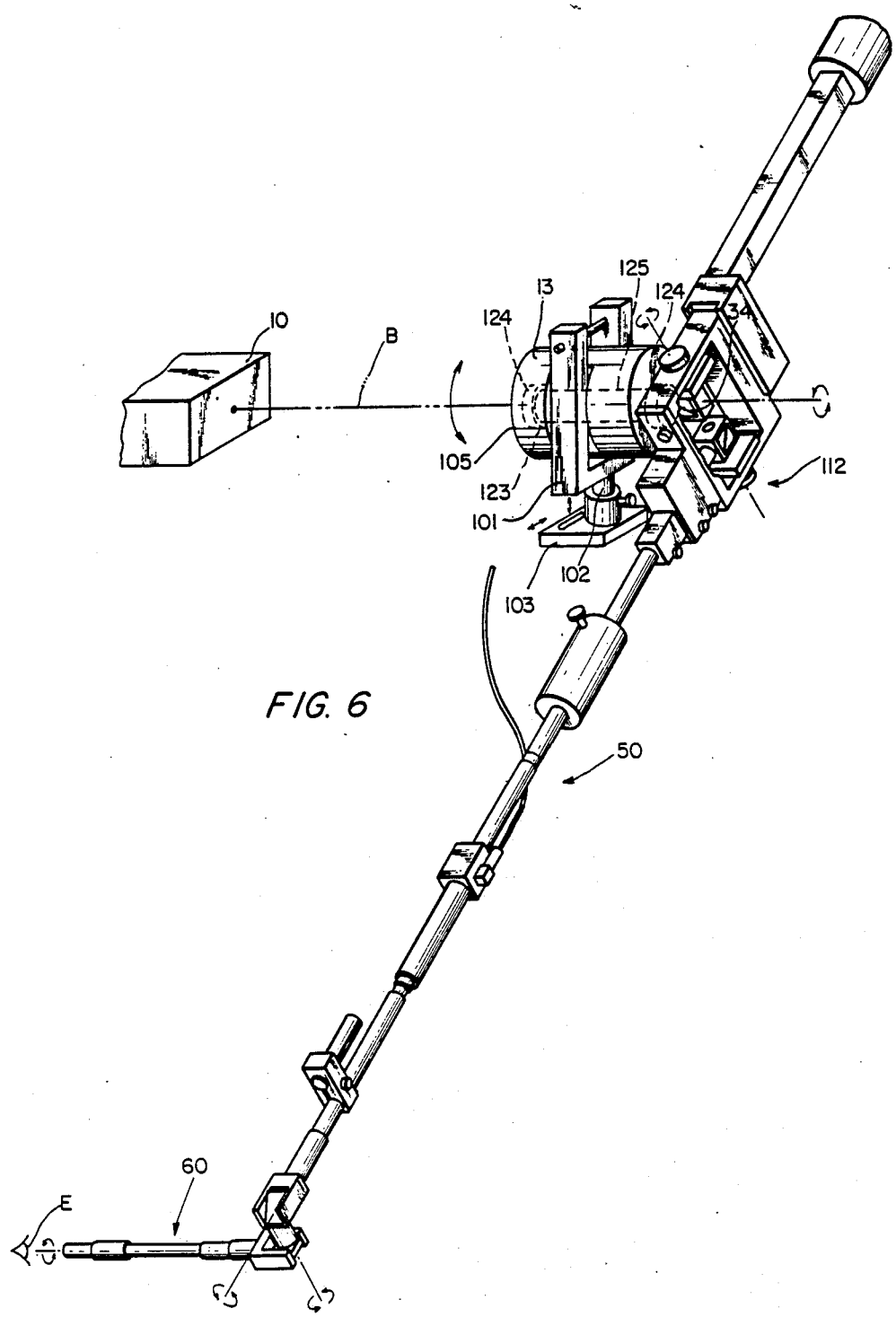
FIG. 6 is a perspective view of an alternate embodiment of the present invention laser delivery system.

Referring now to FIG. 6, there is shown an alternate embodiment of a laser delivery system 112 in accordance with the present invention. The follow, generally cylindrical base 13 is supported by a fork 101, mounted on a post 102 which is axially adjustable and which is mounted on an adjusting plate 103. The base 13 has a lower bearing 123 in an opening 124 in the bottom plate 105 thereof.

A shaft 125 of hollow cylindrical construction is provided, journalled the bearings 123 and 124, and the laser beam B, emitted by the laser 10, will pass into the base 13 and into and through the shaft 125, being reflected by prism 34 as in the embodiment of FIGS. 1-5.

As will be appreciated, the laser embodiment of FIG. 6 does not require a cranked shaft in the base 13, and does not require a prism in the base, such as prism 17 which is present in the embodiment of FIGS. 1-5.

The other portions of the laser delivery system 112 shown in FIG. 6 are the same as in the embodiment of FIGS. 1-5, the system 112 being shown for performing surgery on the eye E of a patient.

The claims and the specification describe the invention presented and the terms that are employed, in the claims draw their meaning from the use of such terms in the specification. Some terms employed in the prior art may be broader in meaning than specifically employed herein. Whenever there is a question between the broader definition of such term as used in the prior art and the more specific use of the term herein, the more specific meaning is meant.

What is claimed is:

1. A laser delivery system comprising:
   (a) a hollow base comprising an opening for receiving a beam,
   (b) a boom support adjacent said base,
   (c) means for mounting said boom support for rotation on a first axis extending through said base, and for rotation on a second axis transverse to said first axis comprising:
      i. a pair of spaced bearings in said based,
      ii. a shaft journalled in said bearings,
      iii. a fork carried by said shaft, and
      iv. bearing means for journalling said boom support on said fork,
   (d) a hollow linear boom having a proximal end and a distal end,
   (e) means for attaching the proximal end of said boom to said boom support,
   (f) said boom comprising boom bearing means permitting axial and rotational movement of said distal end relative to said proximal end,
   (g) a handpiece,
   (h) means for connecting said handpiece to said boom distal end for rotation about an axis transverse of the boom axis, and
   (i) means for conducting a beam from said opening into and through said boom and into said handpiece in all positions of said boom and handpiece.

2. The laser delivery system of claim 1, and further comprising counterweight means for counterbalancing said handpiece comprising a mass having the center of gravity thereof offset from the boom axis oppositely to said handpiece.

3. The laser delivery system of claim 1, and further comprising counterweight means for counterbalancing a part of said boom and said handpiece comprising a first mass on said boom between said boom support and said boom bearing means.

4. The laser delivery system of claim 3, said mass having the center of gravity thereof substantially at the axis of said boom.

5. The laser delivery system of claim 1, and counterweight means for counterbalancing said boom comprising a first mass on the opposite side of said first and second axes from said boom.

6. The laser delivery system of claim 5, and further comprising counterweight means for counterbalancing a part of said boom and said handpiece comprising a second mass smaller than said first mass on said boom between said boom support and said boom bearing means.

7. The laser delivery system of claim 6, said mass having the center of gravity thereof substantially at the axis of said boom.

8. The laser delivery system of claim 5, and further comprising counterweight means for counterbalancing said handpiece comprising a third mass having the center of gravity thereof offset from the boom axis oppositely to said handpiece.

9. The laser delivery system of claim 8, said boom comprising inner and outer telescopic tubular elements, and bearing means for providing a layer of fluid between said inner tubular element and said outer tubular element for supporting said inner tubular element in radially spaced relation to said outer tubular element.

10. The laser delivery system of claim 1, said boom comprising inner and outer telescopic tubular elements, and bearing means for providing a layer of fluid between said inner tubular element and said outer tubular element for supporting said inner tubular element in radially spaced relation to said outer tubular element.

11. The laser delivery system of claim 1, said shaft having first and second aligned portions and an axially offset intermediate portion therebetween, said beam conducting means comprising means in alignment with said opening and said aligned shaft portions for changing the direction of said beam.

12. The laser delivery system of claim 11, said beam conducting means further comprising second and third means carried by said fork for changing the direction of said beam.

13. The laser delivery system of claim 1, a said bearing being in said opening, said beam conducting means comprising a passage through said shaft.

14. The laser delivery system of claim 13, said beam conducting means further comprising first and second means carried by said fork for changing the direction of said beam.

15. A laser delivery system comprising:
   a linearly extending hollow boom having proximal and distal ends,
   means for mounting said boom at the proximal end thereof for rotation about a first axis transverse to the axis of said boom, and a second axis spaced from said boom axis and transverse to said first axis and in a plane perpendicular to said first axis,
   a linear handpiece at the distal end of said boom,
   means for connecting said handpiece to the distal end of said boom for rotation about a first axis perpendicular to said handpiece axis and to the boom axis,
   bearing means for enabling said connecting means and said handpiece to rotate about the axis of said boom,
   first counterweight means for counterbalancing said boom comprising a first mass on the opposite side of said first and second axes from said boom,
   second counterweight means for counterbalancing a portion of said boom and said handpiece comprising a second mass smaller than said first mass,
   third counterweight means for counterbalancing a portion of sid boom and said handpiece comprising a third mass smaller than said second mass and further from said first axis than said second mass and having the center of gravity thereof offset from the boom axis oppositely to said handpiece, and means for conducting a beam sequentially along said second and first axes, said boom, and into said handpiece.

16. The laser delivery system of claim 15, said first counterweight means comprising means for adjusting the position of said first mass relative to said first axis.

17. The laser delivery system of claim 16, said second counterweight means comprising means for adjusting the position of said second mass relative to said first axis.

18. The laser delivery system of claim 15, said second counterweight means comprising means for adjusting the position of said second mass relative to said first axis.

19. The laser delivery system of claim 15, said second counterweight means comprising means for positioning the center of gravity of said second mass substantially at the boom axis.

20. The laser delivery system of claim 19, said second counterweight means comprising means for adjusting the position of said second mass along said boom axis.

21. The laser delivery system of claim 15, said third counterweight means comprising means for adjusting the position of said third mass along the boom axis.

22. The laser delivery system of claim 21, said third counterweight means further comprising means for adjusting the position of said third mass about said boom axis.

23. The laser delivery system of claim 15, said first counterweight means comprising means for adjusting the position of said first mass relative to said first axis, said second counterweight means comprising means for adjusting the position of said second mass relative to said first axis, the center of gravity of said second mass being substantially at the boom axis, and said third counterweight means further comprising means for adjusting the position of said third mass about said boom axis.

24. A laser delivery system comprising:
a linearly extending hollow boom having proximal and distal ends,
a handpiece,
means for connecting said handpiece to said boom distal end for rotation about the axis of said boom, and
counterweight means for counterbalancing said handpiece comprising a mass having the center of gravity thereof offset from the boom axis oppositely to said handpiece.

25. The laser delivery system of claim 24, said counterweight means comprising means for adjusting the position of said mass along the boom axis.

26. The laser delivery system of claim 25, said counterweight means further comprising means for adjusting the position of said mass about said boom axis.

27. A laser delivery system comprising:
a tubular boom having a distal end and a proximal end,
a handpiece at the distal end,
means for conducting a beam into said proximal end, through said boom and into said handpiece,
means for connecting said distal end of said tubular boom to said proximal end of said tubular boom for axial and rotational movement relative thereto comprising inner and outer telescopic tubular elements, and
means for providing a layer of fluid between said inner tubular element and said outer tubular element for supporting said inner tubular element in radially spaced relation to said outer tubular element.

28. The laser delivery system of claim 27, wherein said bearing means comprises axially and circumferentially distributed apertures through said outer element and means to supply fluid under pressure to said openings.

29. The laser delivery system of claim 28, said last mentioned means comprising means providing a plenum chamber radially outwardly of said outer element and the apertures therein, and having inlet means for fluid thereinto.

30. The laser delivery system of claim 29, said fluid supply means further comprising an annular chamber of axial length less than said plenum chamber around said plenum chamber, and aperture means fluid connecting said annular chamber to said plenum chamber.

31. A structure for providing relative linear and rotational movement between tubular elements comprising:
an outer tubular element and an inner tubular element therein and substantially coaxial therewith,
bearing means for providing a layer of fluid between said inner tubular element and said outer tubular element for supporting said inner tubular element in radially spaced relation to said outer tubular element, said bearing means comprising axially and circumferentially distributed apertures through said outer element, and
means for supplying fluid under pressure to said apertures.

32. The structure of claim 31, said last mentioned means comprising means providing a plenum chamber radially outwardly of said outer element and the apertures therein, and having inlet means for fluid thereinto.

33. The structure of claim 32, said fluid supply means further comprising an annular chamber of axial length less than said plenum chamber around said plenum chamber, and aperture means fluid connecting said annular chamber to said plenum chamber.

34. A laser delivery system comprising:
(a) a hollow linear boom comprising an outer telescopic tubular element having a proximal end and an inner telescopic tubular element in said outer telescopic tubular element and having a distal end;
(b) a boom support;
(c) means for mounting said boom support for rotation on a first axis and for rotation on a second axis transverse to said first axis;
(d) means for attaching the proximal end of said boom to said boom support;
(e) said boom comprising boom bearing means for supporting said inner tubular element for axial and rotational movement thereof relative to said outer tubular element without supporting physical bearing engagement;
(f) a handpiece;
(g) means for connecting said handpiece to said boom distal end for rotation about an axis transverse of the boom axis; and
(i) means for conducting a beam through said boom and into said handpiece in all positions of said boom and handpiece.

35. The laser delivery system of claim 34, said bearing means comprising means for providing a layer of fluid between said first and second tubular elements for supporting said inner tubular element in radially spaced relation to said outer tubular element.

36. The laser delivery system of claim 35, wherein said beam conducting means comprises prisms.

37. The laser delivery system of claim 34, wherein said beam conducting means comprises prisms.

38. A laser delivery system comprising:
- a linearly extending hollow boom having proximal and distal ends,
- means for mounting said boom at the proximal end thereof for rotation about a first axis transverse to the axis of said boom, and a second axis spaced from said boom axis and transverse to said first axis and in a plane perpendicular to said first axis,
- a linear handpiece at the distal end of said boom,
- means for connecting said handpiece to the distal end of said boom for rotation about a first axis perpendicular to said handpiece axis and to the boom axis,
- bearing means for enabling said connecting means and said handpiece to rotate about the axis of said boom,
- first counterweight means for counterbalancing said boom comprising a first mass on the opposite side of said first and second axes from said boom,
- second counterweight means for counterbalancing a portion of said boom and said handpiece comprising a second mass on said boom having the center of gravity thereof offset from the boom axis oppositely to said handpiece, and
- means for conducting a beam sequentially along said boom and into said handpiece.

39. The laser delivery system of claim 38, said second counterweight means comprising means for adjusting the position of said second mass along the boom axis.

40. The laser delivery system of claim 39, said second counterweight means further comprising means for adjusting the position of said second means about said boom axis.

41. A laser delivery system comprising:
- a tubular boom having a distal end and a proximal end,
- means at the proximal end of said boom for supporting said boom for pivotal movement,
- a handpiece at the distal end,
- means for conducting a beam into said proximal end, through said boom and into said handpiece, and
- means for connecting said distal end of said tubular boom to said proximal end of said tubular boom for axial and rotational movement relative thereto comprising inner and outer telescopic tubular elements and bearing means for supporting said inner tubular element in radially spaced relation to said outer tubular element without supporting physical engagement.

42. A laser delivery system of claim 41, wherein said bearing means comprises means for providing a layer of fluid between said inner tubular element and said outer tubular element comprising apertures through said outer member.

43. A structure for providing relative linear and rotational movement between tubular elements comprising:
- an outer tubular element,
- an inner tubular element,
- means for holding one said tubular element,
- means for supporting the other said tubular element substantially coaxially with said one tubular element and spaced therefrom without supporting physical engagement,
- said structure being free of means to prevent both axial and rotational movement of said other tubular element relative to said outer tubular element,
- whereby said inner tubular element may be caused to move linearly and to be rotated in said outer tubular element.

* * * * *